United States Patent [19]
Schaumann et al.

[11] Patent Number: 5,989,211
[45] Date of Patent: Nov. 23, 1999

[54] MEDICAL INSTRUMENT FOR SUPPLYING AND REMOVING RINSING FLUID

[75] Inventors: Uwe Schaumann, Villingen-Schwenningen; Rudolf Heimberger, Oberderdingen; Detlef Schweier, Illingen, all of Germany

[73] Assignee: Richard Wolf GmbH, Knittlingen, Germany

[21] Appl. No.: 08/939,849

[22] Filed: Sep. 29, 1997

[30] Foreign Application Priority Data

Nov. 19, 1996 [DE] Germany ............................ 196 47 816

[51] Int. Cl.⁶ .................................................. A61M 1/00
[52] U.S. Cl. .............................. 604/27; 604/19; 604/902; 604/541
[58] Field of Search ................................... 604/19, 27, 35, 604/36, 30, 48, 257, 543, 902, 541

[56] References Cited

U.S. PATENT DOCUMENTS

| | | |
|---|---|---|
| D. 350,194 | 8/1994 | Marino et al. . |
| 4,519,385 | 5/1985 | Atkinson et al. . |
| 5,186,714 | 2/1993 | Boudreault et al. ....................... 604/21 |
| 5,230,704 | 7/1993 | Moberg et al. ............................ 604/34 |
| 5,490,836 | 2/1996 | Desai . |
| 5,609,573 | 3/1997 | Sandock ..................................... 604/22 |

FOREIGN PATENT DOCUMENTS

| | | |
|---|---|---|
| 81 36 066 U | 3/1983 | Germany . |
| 43 21 110 A1 | 1/1994 | Germany . |

*Primary Examiner*—Corrine McDermott
*Assistant Examiner*—Cris L. Rodriguez
*Attorney, Agent, or Firm*—Akin, Gump, Strauss, Hauer & Feld, L.L.P.

[57] ABSTRACT

The medical instrument is equipped with a handle and has a shank for supplying and removing rinsing fluid into or out of a hollow cavity inside the body. There are tubings which can be releasably inserted onto connection pieces connected to the shank and which can be fixed on the connection pieces. The handle is formed as a two-part housing, wherein for opening and closing the housing a first housing part is adjustable relative to a second housing part so that with an opened housing the tubings can be pushed or pulled from then freely situated connection pieces and with a closed housing the tubing ends located on the connection pieces are fixed onto the connection pieces with a friction fit by way of the first housing part.

12 Claims, 4 Drawing Sheets

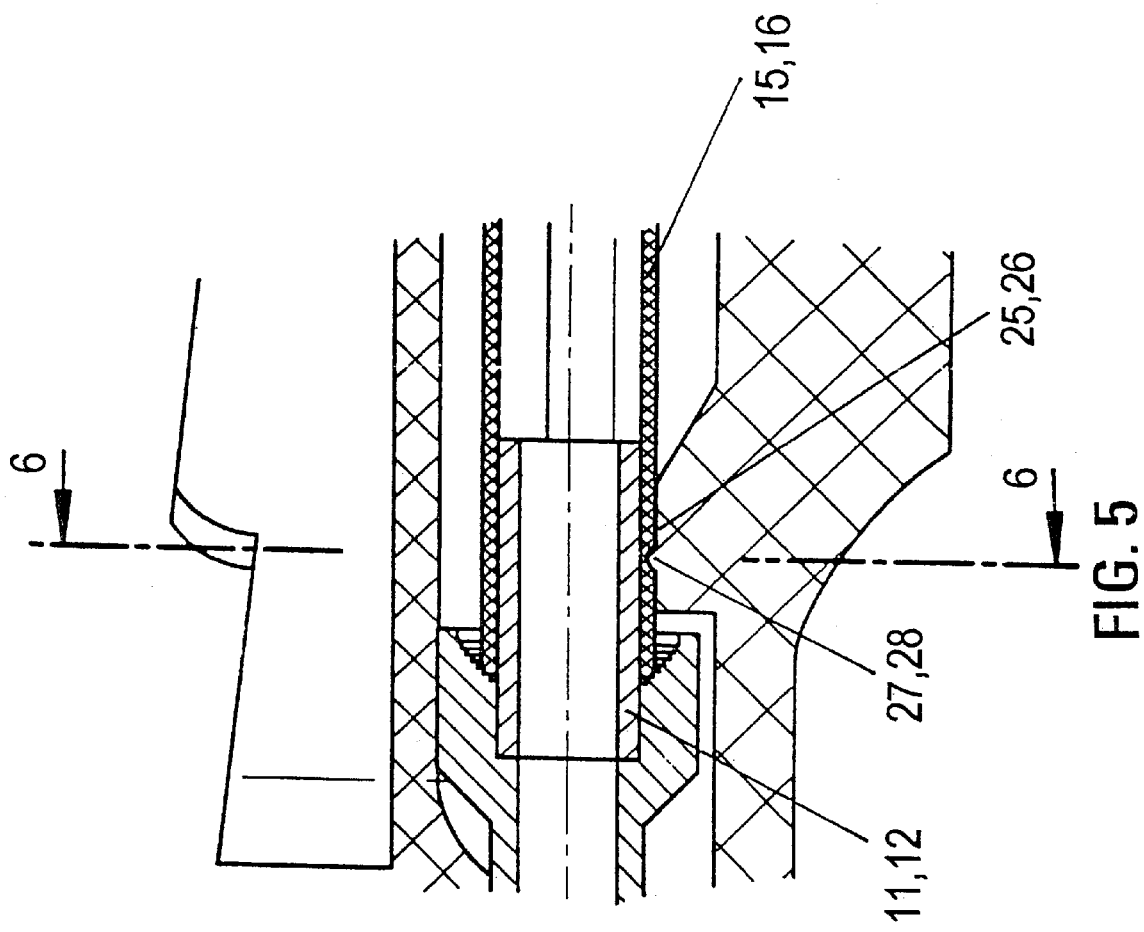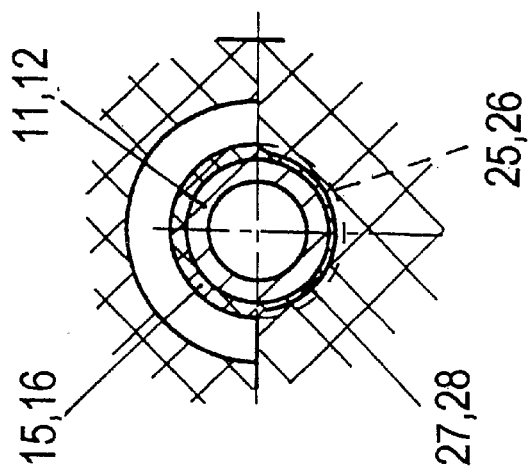

MEDICAL INSTRUMENT FOR SUPPLYING AND REMOVING RINSING FLUID

BACKGROUND OF THE INVENTION

The invention relates to a medical instrument, equipped with a handle, for the delivery and removal of rinsing fluid into or out of a hollow space inside the body via a shank and tubings which are releasably insertable on connection pieces being connected to the shank and which can be fixed onto the connection pieces.

From the German utility model G 81 36 066.3 there is known a medical instrument for the supply and removal of rinsing fluid. The instrument has a shank which can be inserted into a body cavity and comprises a handle through which passes a rinsing and suction channel which are connected to the shank via connection pieces for connecting tubings. The design of this instrument has the objective of being able to connect one and the same handle with various rinsing and suction shanks in a simple way and manner.

SUMMARY OF THE INVENTION

It is the object of the invention to put forward a design solution for an instrument according to the mentioned type which has a connection permitting an easy manufacture and the connection of the tubings supplying and removing the rinsing fluid to the instrument, as well as a secure sealing without additional means.

Proceding from an instrument of the above mentioned type, according to the invention this object is achieved in that the handle is formed as an essentially two-part housing, that for opening and closing the housing a first housing part is adjustable relative to the other second housing part, that with an opened housing the ends of the tubings can be pushed or pulled from connection piece allocated to the second housing part and that with a closed housing the tubing ends are fixed onto the connection pieces with a friction fit by way of the first housing part.

With such a designed instrument the ends of tubings serving to supply and remove the rinsing fluid are freely accessible after opening the housing and are thus easily removed from the connection pieces for the purpose of a required exchange and or cleaning, whilst by closing the housing with the fixing of the tubings onto the connection pieces, a secure sealing is achieved and the tubings in the region of their connections are protected from any inadvertant releasing.

With this, the fixing of the tubing ends onto the connection pieces may be achieved in that the first housing part can be pivoted in and out about a bearing relative to the second housing part which is rigidly connected to the instrument, and that both housing parts with a closed housing or pivoted-in first housing part may be locked. The connection pieces are so arranged in the vicinity of the bearing connecting both housing parts that the parallel longitudinal axes of the connection pieces have a vertical distance to the axis of the bearing, thus do not intersect the bearing axis.

With an equipping of the first housing part with a pressure surface which, on closing the housing by pivoting in the first housing part, can be pressed on the periphery of the tubing ends inserted onto the connection pieces, then on closing the housing by way of the pressure surface additionally a distally directed force component may be brought on the tubing ends having the effect of an increase of the sealing effect. This may be still further improved in that the free ends of the tubings in each case are pushed against truncated cone shaped recesses which are each provided internally at the end of the connection pieces. Furthermore the mentioned displacement of the tubing ends onto the connection pieces may be advantageously aided by forming the pressure surface with a part-annular swelling.

DESCRIPTION OF THE DRAWINGS

The invention is hereinafter described in more detail by way of one embodiment example shown in the drawings. There are shown:

FIG. 5 is a greatly enlarged view of connecting parts of FIG. 3, and

FIG. 6 is a cross-sectional view taken along lines 6—6 in FIG. 5.

DETAILED DESCRIPTION OF THE INVENTION

Figure 1:
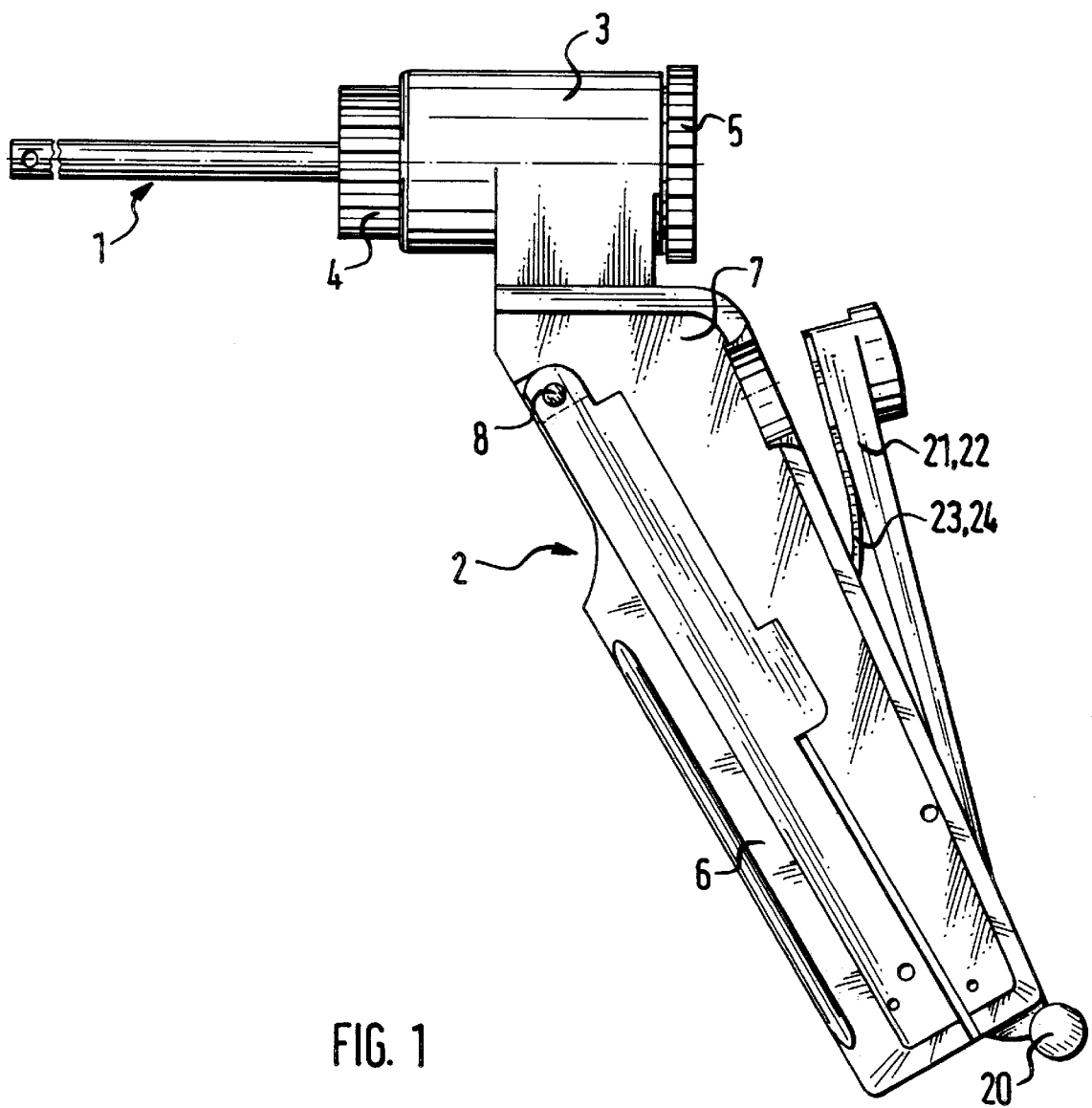
FIG. 1 a complete view of the instrument according to the invention.

The instrument according to the invention, as can best be deduced from FIG. 1, consists essentially of a shank 1 forming a suction and rinsing tube, and of a handle 2.

The shank 1 is releasably fastened in a receiver 3 and for this purpose is fastened to the distal end of the receiver 3 by way of a screw cap 4, the end of the receiver on the proximal side being closed in a fluid tight manner by way of a screwable closing cap 5 for example. Within the receiver 3 there are located channels which are not shown and which by removing the closing cap 5 can be made accessible for example for the purpose of cleaning. At the distal side the channels are connected to the shank 1 which in the known manner may consist of two coaxially arranged shank tubes, so that via one channel and a shank tube rinsing fluid may be supplied and via the other channel and the other shank tube rinsing fluid may be aspirated from the body cavity.

The receiver 3 is connected to the handle 2 in its upper region to a unit, wherein the mentioned channels are led to the connection pieces located in the handle 2. This handle consists of a two-part housing with a first adjustable housing part 6 and a second fixed housing part 7. The first housing part 6 is connected to the second housing part 7 via a bearing 8 located on said second housing part and can be pivoted in and out relative to the housing part 7.

The housing part 7 comprises connecting parts 9, 10 with connection pieces 11, 12 which lie behind one another with respect to the plane of the drawing and which are connected to the channels of the receiver 3 and serve the connection of tubings 15, 16 for the supply and removal of rinsing fluid. The connection pieces 11, 12 are provided with a profile 13 for a better retention and sealing of the tubings 15, 16 and comprise on the distal side a truncated cone shaped recess 17, 18 which at its inner surface likewise has a profile 14.

The second housing part 7 at its lower end is equipped with a hook-shaped closing element 19 which in the closing position of the housing parts 6 and 7 (FIG. 1) effects their mutual locking by way of latching into a suitable latch in the first housing part 6, and can be unlocked via a spring lever 20. On the housing part 7 there are further mounted two operating levers 21, 22 which in the plane of the drawing are arranged displaced behind one another (FIG. 1). The operating levers 21, 22 are in each case allocated to one of the tubings 15, 16 and have compression springs 23, 24 as well as clamping means, not shown, which come into effect alternately with the tubings 15, 16 and with which selectively each tubing may be deformed for closing its passage. In the inoperative position the operating levers 21, 22 project out of the gripping surface caused by the compression springs 23, 24.

Figure 2:
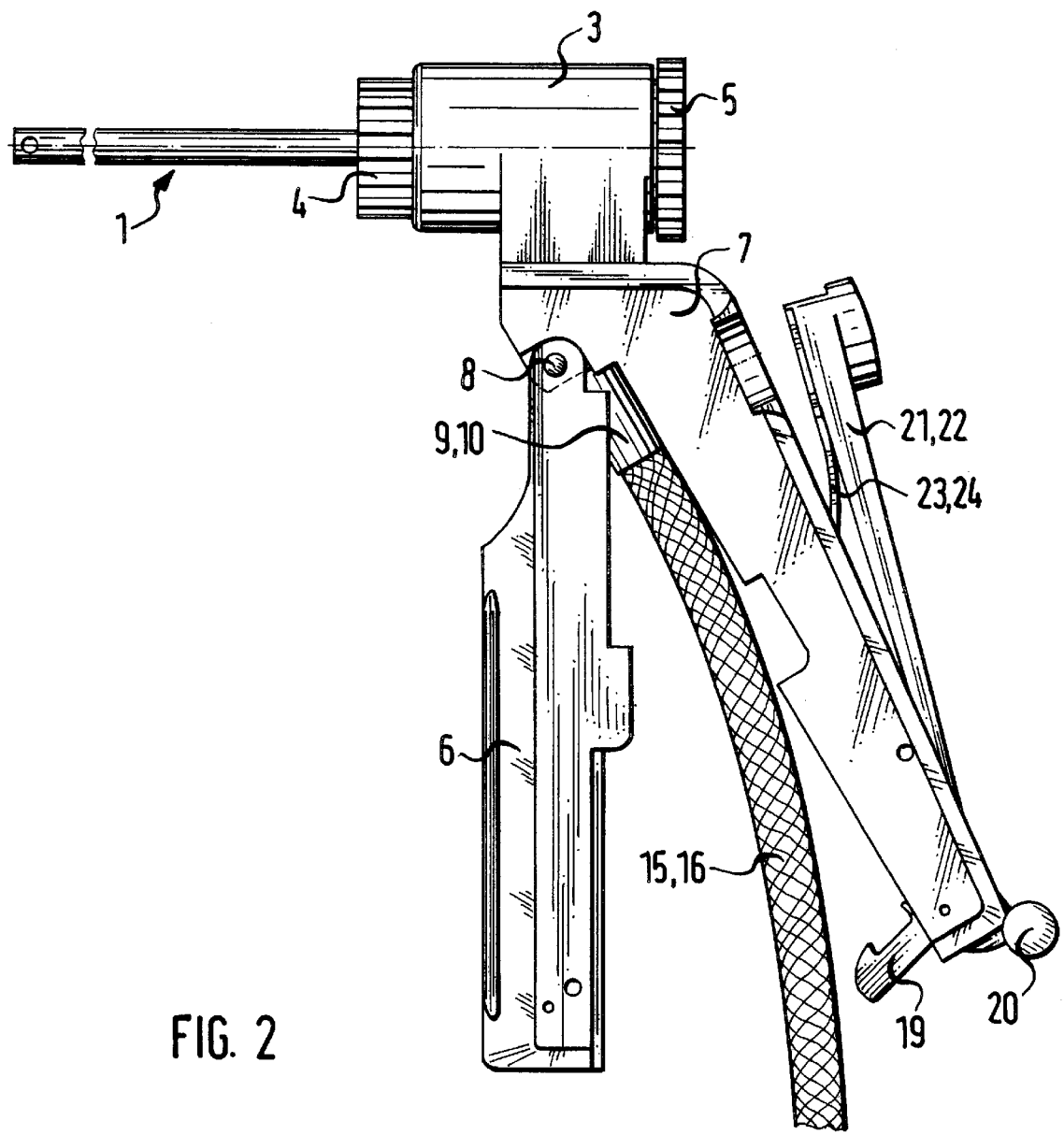
FIG. 2 the instrument according to FIG. 1 with an opened housing.
Figure 3:
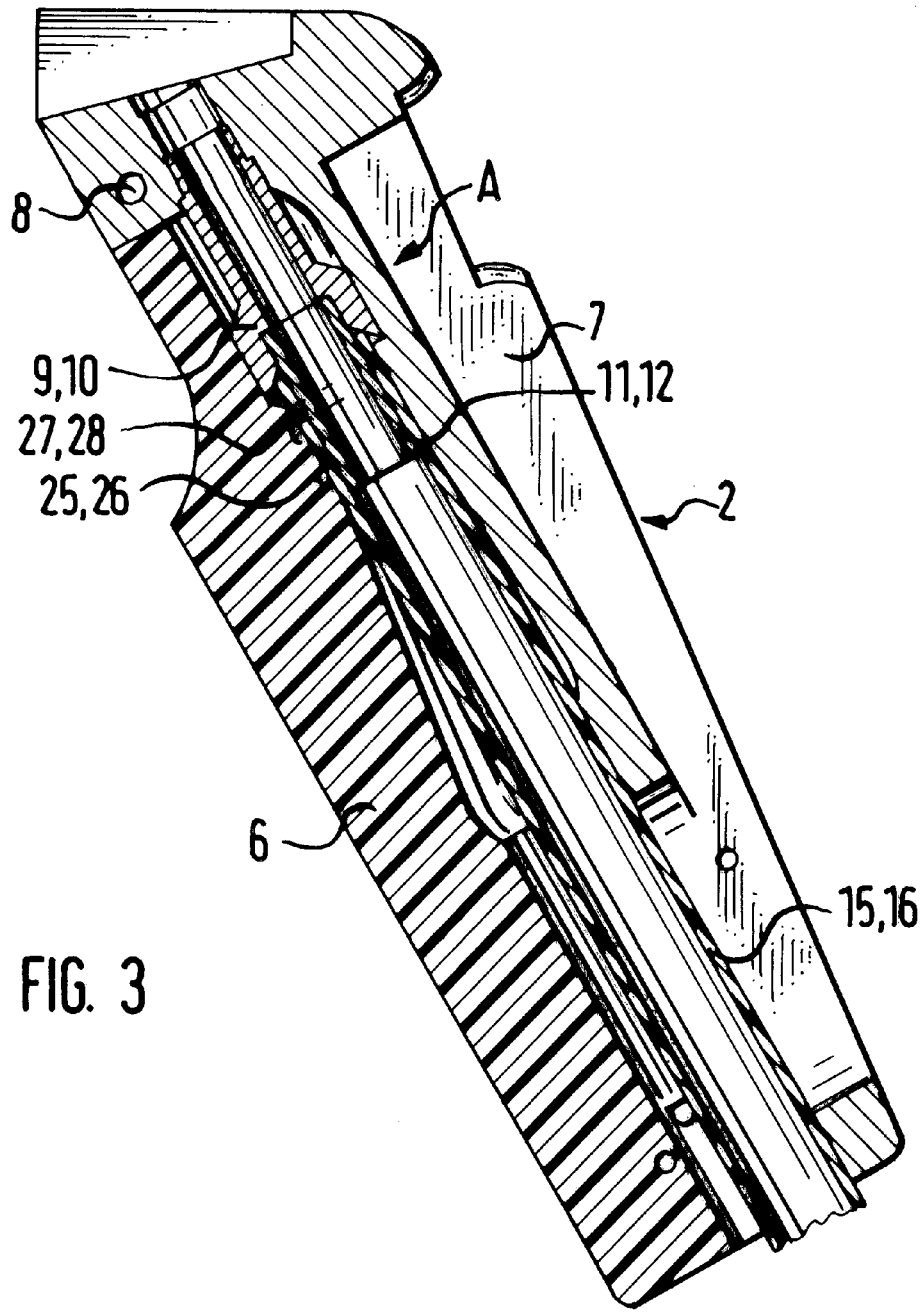
FIG. 3 a longitudinal section through the handle or the housing.
Figure 4:
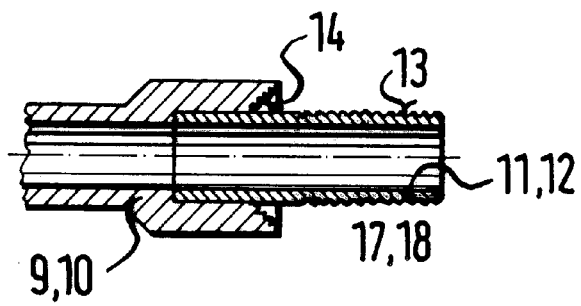
FIG. 4 the detail A of FIG. 3 shown enlarged.

For pulling off or applying the tubings 15, 16 the housing forming the handle 2 is brought into the opening position in which the locking of the housing parts 6 and 7 is released by operating the lever 20 and the housing part 6 is pivoted out (FIG. 2). Then the connection pieces 11, 12 and the ends of the tubings 15, 16 are freely accessible so that these may be easily pulled from the connection pieces or pushed on the connecting pieces.

When applying the tubings it is proceded such that the tubings are pushed so far onto the connection pieces 11, 12 that the respective end face of the tubings 15, 16 respectively comes to rest on the truncated cone shaped recess 17 and 18 of the connecting part 9 and 10. Then by pivoting in the first housing part 6 against the second housing part 7, the housing is closed (FIG. 1), wherein in the end position an automatic mutual locking of the housing parts is effected by way of the closing element 19.

In this position the housing part 6 has partly encompassed the tubings 15, 16 in the region of the connecting pieces 11, 12 in each case with a semi-circular pressing surface 25, 26, wherein furthermore a part-annular swelling 27, 28 in the pressing surface 25, 26 is impressed into the tubing material. The semi-circular pressing surface 25, 26 and the part-annular swelling 27, 28 are shown in detail in FIGS. 5 and 6. With this, the tubing material situated at this location is forced radially against the connection pieces 11, 12 and elastically deformed. The simultaneously arising distally directed displacement of the tubing leads furthermore to a pressing of the end face of the tubings 15, 16 against the truncated cone shaped recess 17, 18 and thus to an effective sealing, since due to the part annular swelling 27, 28, a distally directed pushing force engages on the tubings 15, 16. This arises due to the fact that the bearing 8 connecting the housing parts 6, 7 is arranged at a vertical distance to the longitudinal axes of the connection pieces 11, 12.

Such a prepared instrument may then be applied wherein by operating the levers 21, 22 depending on the operating distance, a narrowing or blocking of the tubings 15, 16 is effected and thus the supply and removal of rinsing fluid may be controlled.

We claim:

1. A medical instrument for supplying and removing rinsing fluid into or out of a hollow cavity inside a body, comprising a shank and a handle connected to the shank, connection pieces connected to the handle, tubings having ends releasably connectable to the connection pieces which are fixable on the connection pieces, the handle comprising a two-part housing having a first housing part and a second housing part, the first housing part is adjustable between an open position and a closed position relative to the second housing part, in the open position the ends of the tubings can be pushed or pulled from the connection pieces and in the closed position the tubing ends are fixed onto the connection pieces with a friction fit by way of the first housing part contacting the tubings.

2. An instrument according to claim 1, wherein the first housing part is pivotably connected to the second housing part by a bearing, the second housing part is rigidly connected to an operating instrument, and the first and second housing parts may be locked together in the closed position.

3. An instrument according to claim 2, wherein the connection pieces are provided in a vicinity of the bearing and wherein the connection pieces have parallel longitudinal axes which are offset a vertical distance to an axis of the bearing.

4. An instrument according to claim 3, wherein the first housing part is equipped with a pressure surface which in the closed position presses onto a periphery of the tubing ends inserted onto the connection pieces.

5. An instrument according to claim 3, wherein the connection pieces are inserted into connecting parts having tubing side ends, a truncated cone shaped recess for receiving the free end of the tubing is internally formed on the tubing side ends.

6. An instrument according to claim 2, wherein the first housing part is equipped with a pressure surface which in the closed position presses onto a periphery of the tubing ends inserted onto the connection pieces.

7. An instrument according to claim 2, wherein the connection pieces are inserted into connecting parts having tubing side ends, a truncated cone shaped recess for receiving the free end of the tubing is internally formed on the tubing side ends.

8. An instrument according to claim 1, wherein the first housing part is equipped with a pressure surface which in the closed position presses onto a periphery of the tubing ends inserted onto the connection pieces.

9. An instrument according to claim 8, wherein the pressure surface is provided with a part-annular swelling.

10. An instrument according to claim 9, wherein the connection pieces are inserted into connecting parts having tubing side ends, a truncated cone shaped recess for receiving the free end of the tubing is internally formed on the tubing side ends.

11. An instrument according to claim 8, wherein the connection pieces are inserted into connecting parts having tubing side ends, a truncated cone shaped recess for receiving the free end of the tubing is internally formed on the tubing side ends.

12. An instrument according to claim 1, wherein the connection pieces are inserted into connecting parts having tubing side ends, a truncated cone shaped recess for receiving the free end of the tubing is internally formed on the tubing side ends.

* * * * *